(12) United States Patent
Barandun et al.

(10) Patent No.: US 11,523,709 B2
(45) Date of Patent: Dec. 13, 2022

(54) FRYING UNIT

(71) Applicant: FFM PROJEKT AG, Wil (CH)

(72) Inventors: Urs Barandun, Stettfurt (CH); Cyrill Binder, Zürich (CH)

(73) Assignee: FFM PROJEKT AG, Wil (CH)

( * ) Notice: Subject to any disclaimer, the term of this patent is extended or adjusted under 35 U.S.C. 154(b) by 65 days.

(21) Appl. No.: 16/643,493

(22) PCT Filed: Aug. 23, 2018

(86) PCT No.: PCT/EP2018/072730
§ 371 (c)(1),
(2) Date: Feb. 28, 2020

(87) PCT Pub. No.: WO2019/042852
PCT Pub. Date: Mar. 7, 2019

(65) Prior Publication Data
US 2020/0345179 A1    Nov. 5, 2020

(30) Foreign Application Priority Data

Aug. 29, 2017 (CH) .................................... 01066/17

(51) Int. Cl.
*A47J 37/12* (2006.01)
*A23L 3/36* (2006.01)
(Continued)

(52) U.S. Cl.
CPC ........... *A47J 37/1228* (2013.01); *A23L 3/361* (2013.01); *A23L 3/365* (2013.01); *A47J 37/1214* (2013.01);
(Continued)

(58) Field of Classification Search
CPC .. A47J 37/1219; A47J 37/1228; A47J 37/129; A47J 37/1295
(Continued)

(56) References Cited

U.S. PATENT DOCUMENTS 3,505,072 A  *  4/1970  Rullman  ............. A47J 37/1214
                                                         99/336
3,894,483 A      7/1975  Anetsberger et al.
(Continued)

FOREIGN PATENT DOCUMENTS

KR     1020120119002 A  * 10/2012  .......... A47J 37/1219
KR         101214519      * 12/2012  .......... A47J 37/1219
(Continued)

OTHER PUBLICATIONS

International Search Report and Written Opinion for related PCT App No. PCT/EP2018/072730 dated Nov. 30, 2018, 21 pgs.
(Continued)

*Primary Examiner* — Reginald Alexander
(74) *Attorney, Agent, or Firm* — Procopio, Cory, Hargreaves & Savitch, LLP

(57) ABSTRACT

A frying unit, comprising an oil pan (1) which is essentially open on top, a transport unit (2), using which a basket (3) is movable from a filling position into the interior of the oil pan (1) and using which the basket (3) is movable from the interior of the oil pan (1) into an emptying position, wherein the oil pan (1) is designed in such a way that it can accommodate multiple baskets (3) simultaneously, and the transport unit (2) is designed in such a way that the baskets (3) are movable independently of one another.

16 Claims, 6 Drawing Sheets

(51) Int. Cl.
| | |
|---|---|
| *A23L 3/365* | (2006.01) |
| *G01K 13/00* | (2021.01) |
| *G01N 33/03* | (2006.01) |
| *G07F 9/10* | (2006.01) |
| *G07F 17/00* | (2006.01) |
| *G01G 13/00* | (2006.01) |

(52) U.S. Cl.
CPC ....... *A47J 37/1219* (2013.01); *A47J 37/1223* (2013.01); *A47J 37/1257* (2013.01); *A47J 37/1271* (2013.01); *A47J 37/1295* (2013.01); *G01K 13/00* (2013.01); *G01N 33/03* (2013.01); *G07F 9/105* (2013.01); *G07F 17/0085* (2013.01); *A23V 2002/00* (2013.01); *G01G 13/00* (2013.01)

(58) Field of Classification Search
USPC .......................................................... 99/407
See application file for complete search history.

(56) References Cited

U.S. PATENT DOCUMENTS

| | | |
|---|---|---|
| 5,125,328 A | 6/1992 | Grandi |
| 8,584,579 B1 | 11/2013 | Sumner, Sr. |

FOREIGN PATENT DOCUMENTS

| | | |
|---|---|---|
| KR | 101518780 B1 | 5/2015 |
| WO | 9109558 A1 | 7/1991 |
| WO | 2010044258 A1 | 4/2010 |

OTHER PUBLICATIONS

International Preliminary Report on Patentability for related PCT App No. PCT/EP2018/072730 dated Mar. 12, 2020, 13 pgs.

* cited by examiner

FRYING UNIT

CROSS-REFERENCE TO RELATED APPLICATIONS

This application is a U.S. National Stage entry of PCT Application No: PCT/EP2018/072730 filed on Aug. 23, 2018, which claims priority to CH Patent Application No. 01066/17, filed Aug. 29, 2017, the contents of which are incorporated herein by reference.

TECHNICAL AREA

The present invention relates to a frying unit, in particular for frying portioned piece goods and bulk goods.

PRIOR ART

An automatic deep fryer is known from US 2016/0278577, in which a basket can be filled at a filling station, wherein the basket is movable after the filling by means of a transport unit to one of multiple frying units and after the frying into an emptying position. The frying units are separate from one another and each frying unit can only accommodate one basket at a time for frying. Each frying unit has to be heated separately and the quality of the frying oil is to be ensured separately in each frying unit. The large distances between the frying units and the filling or emptying positions, respectively, result in long process paths of the transport unit, whereby long waiting times result. The long movement paths have to be taken into consideration in the frying times of the individual frying units, since otherwise the material to be fried is fried too long and chars. This results in long waiting times for the user of such an automatic deep fryer if multiple orders are placed in succession.

DESCRIPTION OF THE INVENTION

One object of the present invention is to provide a simple and cost-effective frying unit, using which the above-mentioned disadvantages can be avoided.

This object is achieved by a frying unit having the features of claim 1. Further embodiments of the frying unit, an automatic deep fryer having a frying unit according to the invention, and a method for frying piece goods are defined by the features of further claims.

A frying unit according to the invention, comprising
an oil pan which is essentially open on top,
a transport unit using which a basket is movable from a filling position into the interior of the oil pan and using which the basket is movable from the interior of the oil pan into an emptying position,
characterized in that the oil pan is designed in such a way that it can accommodate multiple baskets simultaneously, and the transport unit is designed in such a way that the baskets are movable independently of one another.

Therefore, multiple baskets can be immersed in the common oil pan in rapid succession, which permits at least partially simultaneous frying. The oil pan can be dimensioned in such a way that two, three, four, five, six, or more baskets can be arranged adjacent to one another therein. In a common oil pan, the total volume of the oil which can be accommodated therein is greater, whereby a more uniform oil temperature and/or oil quality is achievable. Due to the independent movability of the baskets with the transport unit, different material to be fried and/or different quantities of material to be fried can be optimally fried independently of one another. The transport unit can be designed in such a way that one, two, three, four, or more baskets can be moved and/or transported simultaneously and independently of one another. It is also possible to design the transport unit in such a way that groups of baskets are movable independently of one another, wherein a group of baskets can comprise two, three, four, or more baskets.

In one embodiment, the oil pan comprises a bottom and side walls adjoining thereon which are closed per se. In the interior of the oil pan, spaced apart from the bottom and the side walls, a heating coil is provided, using which oil is heatable which is located in the oil pan. The heating coil can be arranged completely in the interior of the oil pan, wherein electrical lines are led from the heating coil to an exterior of the oil pan. Alternatively, the heating coil can lead from the exterior of the oil pan into its interior. Multiple heating coils can be provided in different regions of the oil pan. The different regions can be separated from one another by partition walls in an at least partially sealed manner. A zone having cooler oil can form below the heating coil due to the distance of the heating coil from the bottom. If parts separate from the material to be fried during the frying, they then generally sink down. Due to the sinking, they reach the zone having cooler oil, whereby it is possible to prevent the parts from completely charring. This has a positive effect on the oil quality, since the charring negatively influences the taste of the frying oil and thus of the material to be fried. The oil pan can be insulated, whether by enclosing it using a layer made of insulation material and/or by embodying it as double-walled.

In one embodiment, the oil pan comprises basket receptacles in which the baskets can be accommodated, wherein the baskets can be arranged in upper basket receptacles above the oil which is located in the oil pan, and wherein the baskets can be arranged in lower basket receptacles in this oil. Different basket receptacles can be provided at different distances to the bottom of the oil pan, wherein the immersion depth of the baskets may be set by the distance to the bottom. The basket receptacles can be arranged fixedly or movably on the oil pan. For example, a basket receptacle can be moved away from the pan bottom if the immersion depth of a basket arranged therein is to be reduced. A smaller quantity of material to be fried requires a lesser immersion depth. The baskets can be arranged in the upper basket receptacles for the dripping off of the frying oil. The baskets can also be arranged in the upper basket receptacles when they are not needed. In this case, the upper basket receptacles are used as storage locations. For example, the upper and/or lower basket receptacles can comprise recesses which taper toward the bottom of the oil pan. The baskets are thus centered and securely held in the receptacles.

In one embodiment, the transport unit comprises a vertical guide, a vertical drive, and a horizontal drive, using which a basket holder is movable horizontally and/or vertically, wherein a basket can be releasably held using the basket holder. The transport unit can also comprise multiple horizontal and/or vertical guides and drives. Multiple basket holders can also be provided, which are movable individually or in groups. It is also conceivable that one vertical guide and one vertical drive are combined with multiple horizontal guides and horizontal drives, or multiple vertical guides and multiple vertical drives are combined with one horizontal guide and one horizontal drive. The basket holder can be designed to be pivotable or clampable.

In one embodiment, the vertical drive and/or the horizontal drive is a drive which is selectable from a group which comprises spindle drives, belt drives, chain drives, linear motors, linear cylinders, and the like.

In one embodiment, the frying unit comprises at least one basket, wherein the basket comprises a bottom and side walls adjoining thereon and on one another, which are at least partially oil-permeable. A holder is provided at an upper end of the basket, which can be held by the basket holder. A receptacle element is provided at a lower end of the basket, which can be accommodated in the basket receptacles. The holder can be arranged in an upper region of a side wall. The receptacle element can be arranged in a lower region of the side wall, on which the holder is arranged, and/or on a side wall opposite thereto. Alternatively or additionally, at least one receptacle element can be arranged on the side walls located in between these side walls. Two or more receptacle elements can be provided on one side wall. One or more receptacle elements can also be arranged on the bottom of the basket.

In one embodiment, the bottom of the basket is fixedly connected to the side walls or the bottom comprises at least one flap, which is arranged so it is pivotable on one of the side walls. Two or more pivotable flaps can also be provided.

In one embodiment, a first side wall comprises at least one flap, which is arranged so it is pivotable on at least one side wall adjacent to the first side wall or which is arranged so it is pivotable on the bottom. Two or more pivotable flaps can also be provided. Restoring elements, for example, springs, can be provided on all flaps to move the flaps back into the closed position when they are pivoted out of this position.

In one embodiment, the holder comprises two essentially parallel rods, which extend away from the basket. The rods are arranged on a side wall of the basket and extend essentially perpendicularly to this side wall. Each of the rods can be accommodated and/or clamped by the basket holder. Using the two parallel rods, it is possible to prevent the basket from inadvertently rotating around one of its axes during the movement with the transport unit. Instead of the two rods, a holder having a plate or having a profile can also be provided.

In one embodiment, the frying unit comprises an oil processing unit having a discharge line, a filter connected to the discharge line, a pump connected to the filter, and a return line connected to the pump, using which oil can be discharged from the oil pan, filtered, and returned to the oil pan. For example, the discharge line can be arranged in the region of the cold zone, whereby the cooler frying oil can be returned via the filter and the pump by means of the return line back to the oil pan. The return line can be arranged in an upper region of the oil pan.

In one embodiment, one or more sensors can be arranged in or on the oil pan. The sensors can be arranged in a region close to the bottom, a middle region, or an upper region of the oil pan. Temperature sensors and/or oil quality sensors can be provided. The sensors can alternatively or additionally also be provided in the oil processing unit.

In one embodiment, the frying unit comprises an emptying unit, using which fried material can be emptied in the emptying position from the basket.

For example, the emptying unit comprises a pivot unit, using which the basket is pivotable around an axis and/or the emptying unit comprises a flap unit, using which the at least one flap of the basket is actuatable for opening and/or closing. Using the emptying unit, the basket can be pivoted, for example, around one of its horizontal main axes. The pivot angle can be, for example, 90 degrees or 180 degrees. Alternatively or additionally, the at least one flap of the basket can be opened using the emptying unit, i.e., it can be pivoted by an angle of 90 degrees or more. A combination of the pivot movement of the basket with the opening of the flap is also possible. For example, the bottom can be folded open without the basket having to be rotated. Alternatively, a side wall of the basket or a flap arranged therein can be opened and the basket can then be rotated by 90 degrees. In a further alternative, the basket can be rotated by 180 degrees without the bottom or a side wall of the basket being opened.

In one embodiment, the frying unit comprises a cover which can be lowered, using which the oil pan can be at least partially covered. When nothing has to be fried, the cover can be lowered onto the oil pan, whereby it is covered essentially sealed on top. It is thus possible to prevent the oil from being soiled and the heat loss of the oil can be reduced. Moreover, it is possible to prevent oil and/or steam from escaping the region of the oil pan. Alternatively, the cover can be pushed over the oil pan from the side. The cover can be designed in such a way that the baskets which are located in the upper basket receptacles are also covered by the cover. In this case, the cover comprises side walls, which protrude laterally over the baskets and seal against the oil pan. Alternatively, the upper basket receptacles can be arranged over the oil pan and the cover can be pushed over the oil pan below the baskets. The cover can be formed insulated, i.e., provided with an insulation layer or formed double-walled. The cover can furthermore comprise a condensate drain, using which oil and steam which condense on the surface of the cover can be discharged.

In one embodiment, the frying unit comprises a ventilation unit having a fan, a filter, and/or an oil separator. The intake air and/or exhaust air can be processed using the ventilation unit. The processing of the intake air is for reasons of hygiene and the processing of the exhaust air is to reduce or prevent odor emissions to the surroundings.

In one embodiment, the frying unit comprises a housing, which at least partially encloses the above-mentioned components of the frying unit. The housing can be formed essentially closed. It can comprise openings in the region of the filling position and in the region of the emptying position. Material to be fried can be supplied to the frying unit through the opening at the filling position and fried material can be discharged from the frying unit through the opening at the emptying position. The openings can be formed closable. For example, they can be closed using at least one slide or at least one flap. The housing can comprise the above-mentioned ventilation unit. The ventilation unit can comprise multiple fans, filters, and/or oil separators and can be arranged in the region of the filling position or the filling opening and/or in the region of the emptying position or the emptying opening, respectively.

An automatic deep fryer according to the invention comprises
- a housing,
- a metering apparatus, which is arranged in an upper region of the housing,
- a frying unit according to any one of the preceding claims, which is arranged below the metering apparatus,
- wherein piece goods which leave the metering apparatus can reach the frying unit. The piece goods can be conveyed by gravity or by a mechanical conveyor system from the metering apparatus to the frying unit.

In one embodiment, the automatic deep fryer comprises:
- a conveyor unit,
- a removal unit,
- an input unit,
- a payment unit,
- a security unit, and
- a transmission unit.

A method according to the invention for frying piece goods comprises the following steps:
- providing a frying unit according to the invention;
- moving the basket into the filling position;
- filling the basket with piece goods in the filling position;
- moving the basket from the filling position into the interior of the oil pan using the transport unit;
- frying the piece goods in the basket in the interior of the oil pan;
- moving the basket from the interior of the oil pan into an emptying position using the transport unit.

The fried piece goods can be arranged above the oil pan for the frying oil to drip off.

The mentioned embodiments of the frying unit, the automatic deep fryer, and the method for frying piece goods may be used in any arbitrary combination if they do not contradict one another.

BRIEF DESCRIPTION OF THE DRAWINGS

Exemplary embodiments of the present invention are explained in greater detail hereafter on the basis of figures. These serve solely for explanation and are not to be interpreted as restrictive. In the figures.

DETAILED DESCRIPTION OF THE INVENTION

Figure 1:
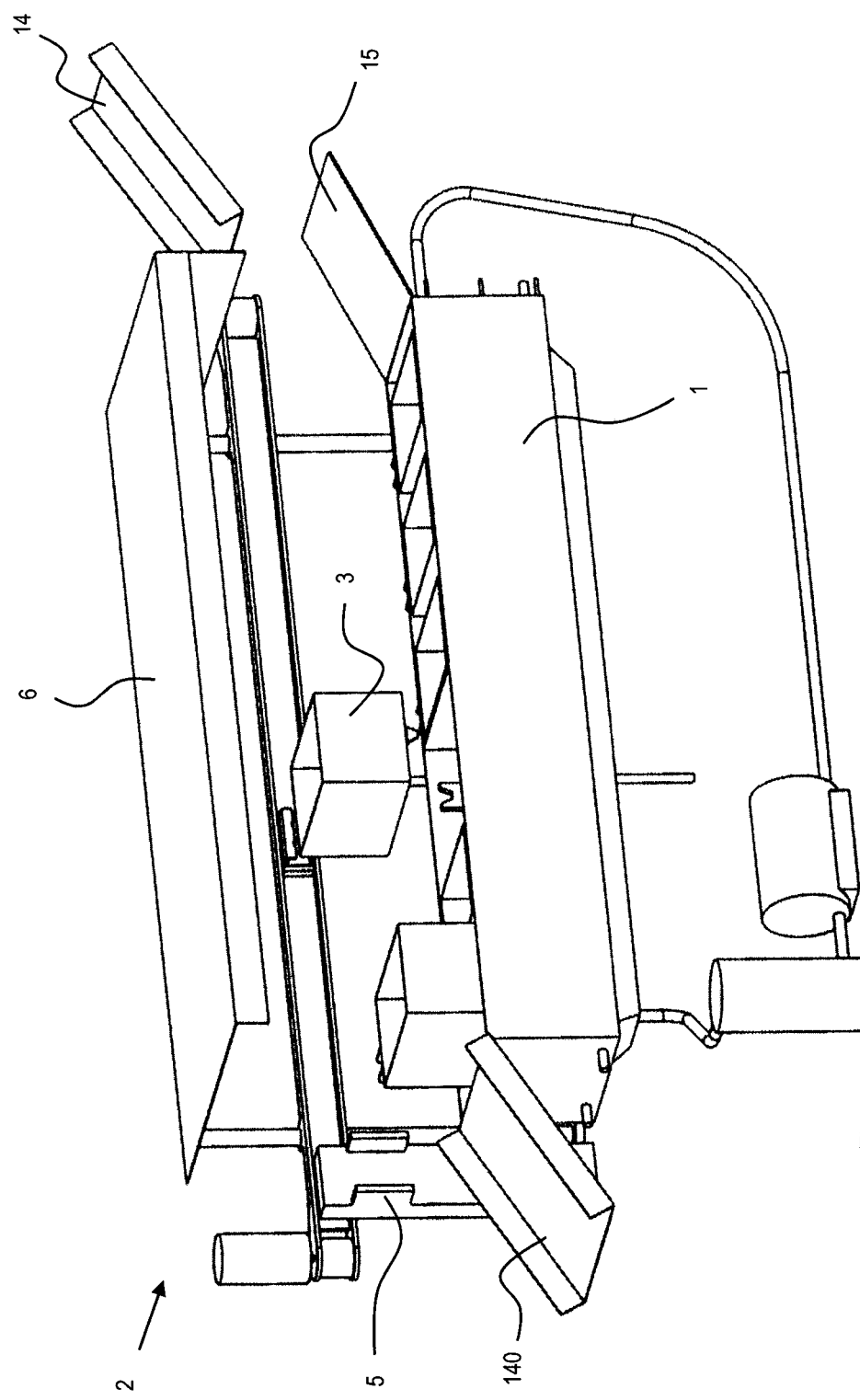
FIG. 1 shows a perspective illustration of a frying unit according to the invention.

FIG. 1 shows a schematic illustration of a frying unit according to the invention. The frying unit essentially comprises an oil pan 1, which is open on top, a transport unit 2, using which baskets 3 are movable from a filling position into the interior of the oil pan 1 and using which the baskets 3 are movable from the interior of the oil pan 1 into an emptying position. The oil pan 1 can accommodate multiple baskets 3 simultaneously. In the illustrated embodiment, six baskets 3 can be accommodated simultaneously. In the filling position, an intake chute 14 is provided, using which it is possible to slide the material to be fried into the basket. In the emptying position, an outlet chute 140 is provided, using which it is possible to guide the fried material out of the basket, for example, to a removal position. A drip plate 15 is provided below the filling position, which conducts oil dripping down, and also parts of the material to be fried which fall out of the baskets, to the oil pan. The frying unit furthermore comprises an oil processing unit 4, using which the quality of the frying oil can be ensured. An emptying unit 5 is provided in the region of the emptying position, using which the fried material located in a basket 3 can be moved onto the outlet chute 140. A cover 6 which can be lowered is provided above the oil pan 1, using which the oil pan 1 can be at least partially covered, i.e., using which the upper opening of the oil pan 1 is closable.

Figure 2:
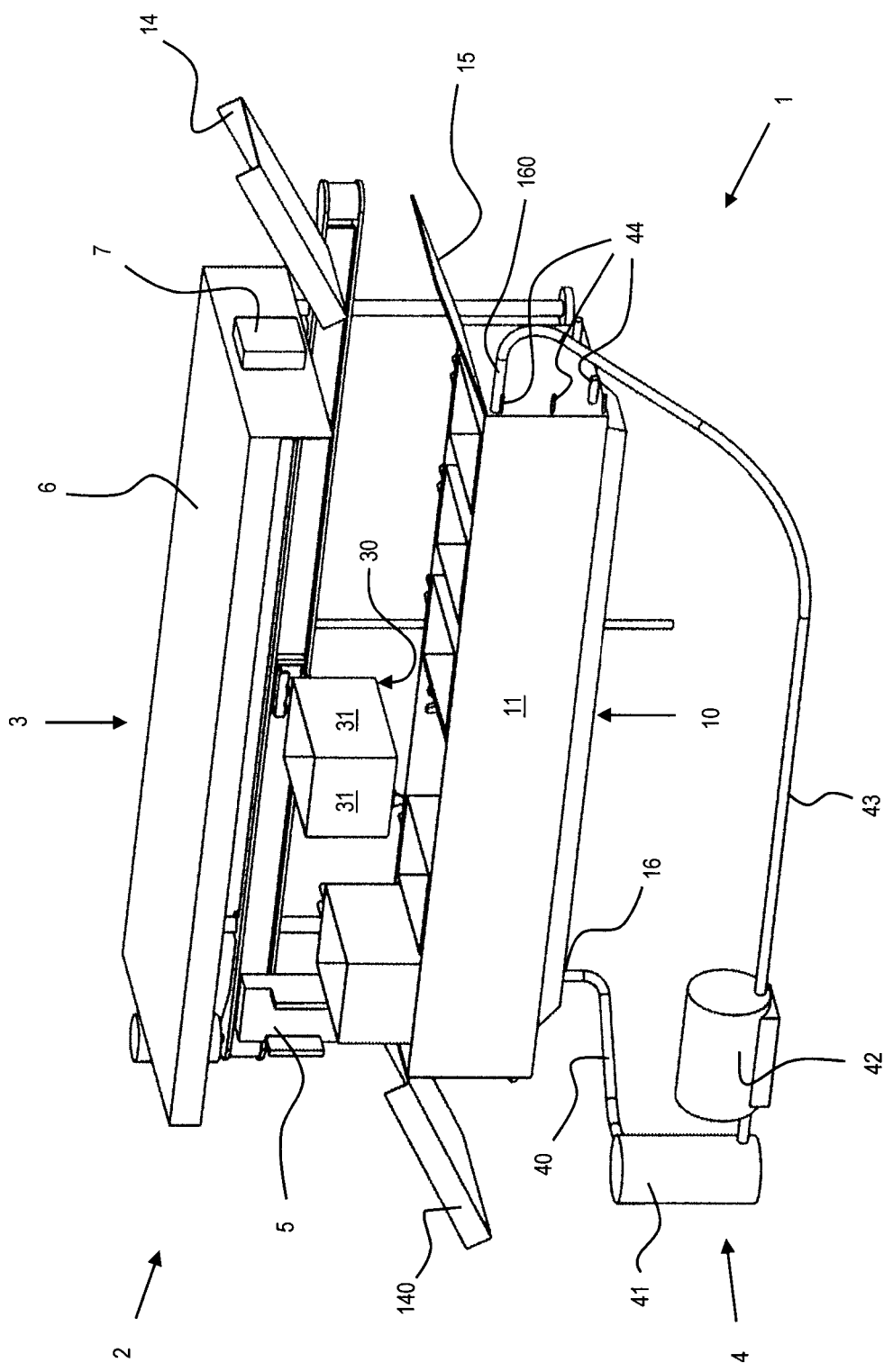
FIG. 2 shows a further perspective illustration of the frying unit of FIG. 1.

FIG. 2 shows a further perspective illustration of the frying unit of FIG. 1. The oil pan 1 comprises a bottom 10 and side walls 11, which are closed per se on the circumference and which extend upward from the bottom 10. Each basket 3 comprises a bottom 30 and side walls 31, which are closed per se on the circumference and which extend upward from the bottom 30. The bottom 30 and the side walls 31 of each basket 3 are oil-permeable. They can be manufactured from a metal mesh, for example, a grating, a perforated plate, or the like. The oil processing unit 4 comprises a discharge line 40, which is connected to an outlet 16. The outlet 16 is arranged on the bottom 10 of the oil pan 1. The discharge line 40 leads to an oil filter 41, which is connected to an oil pump 42. From the pump 42, a return line leads back to an inlet 160 on the oil pan 1. The inlet 160 is arranged in the upper region of a side wall 11 of the oil pan 1. The frying oil can be conveyed and filtered from the oil pan 1 using the oil processing unit 4 in a circuit. The filtration can be carried out continuously or periodically. It can be carried out during the frying or it can be carried out when the frying unit is not in operation, i.e., when the oil is not heated. The filtering can also only be carried out when the frying unit has been unused for a specific time, i.e., when the oil has cooled down below a predetermined temperature. Sensors 44 are provided on the oil pan 1. The illustrated sensors are arranged on a side wall 11 of the oil pan 1 in an upper region, in the middle, and in a lower region. The sensors can be temperature sensors or oil quality sensors. The sensors can also be arranged on the bottom 10 of the oil pan 1 or in the oil processing unit 4. A ventilation system 7 is arranged on the cover 6. The ventilation system 7 comprises a fan or ventilator and can additionally also comprise a separator for steam and/or oil.

Figure 3:
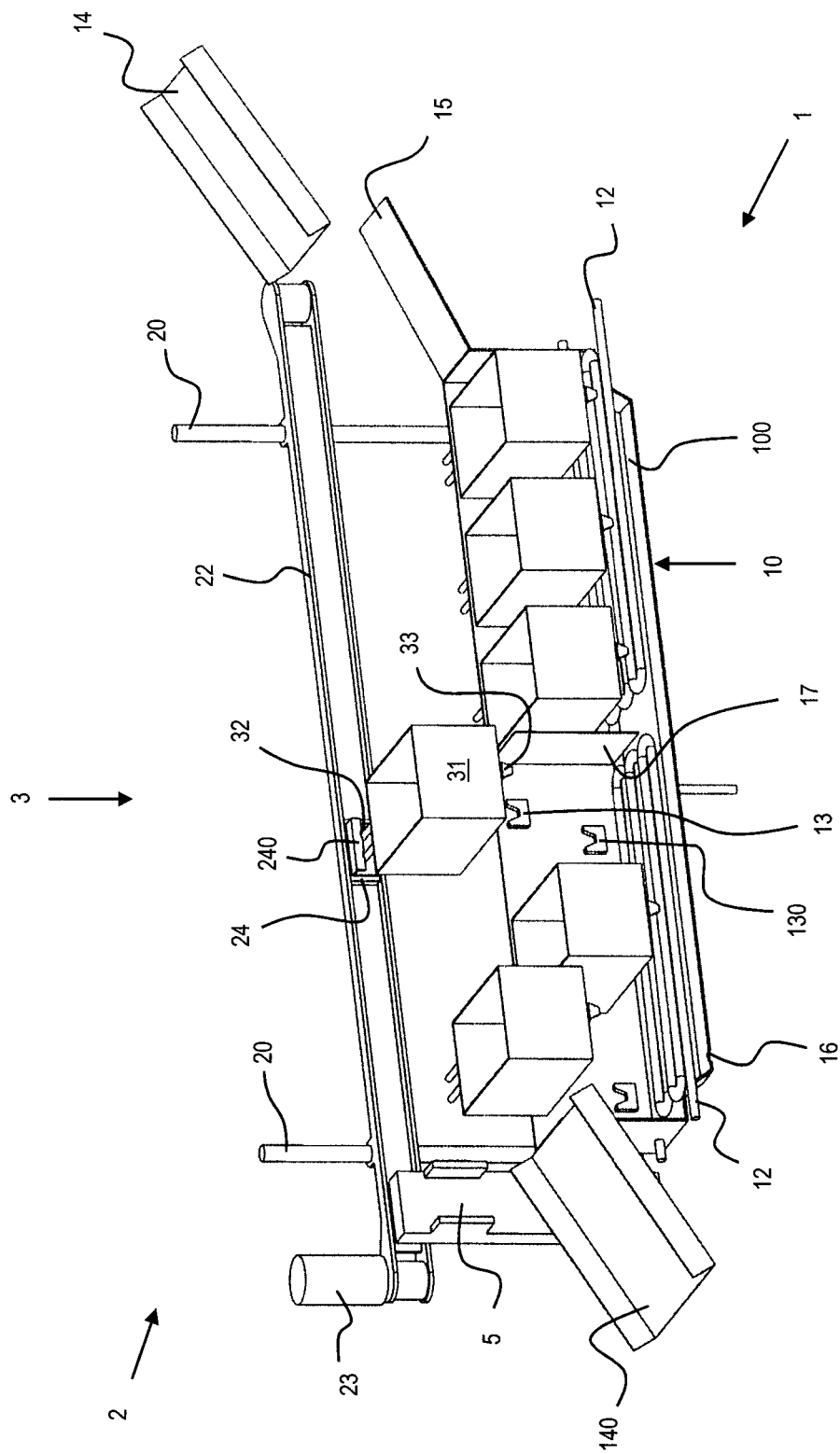
FIG. 3 shows a perspective sectional view of the frying unit of FIG. 1.
Figure 4:
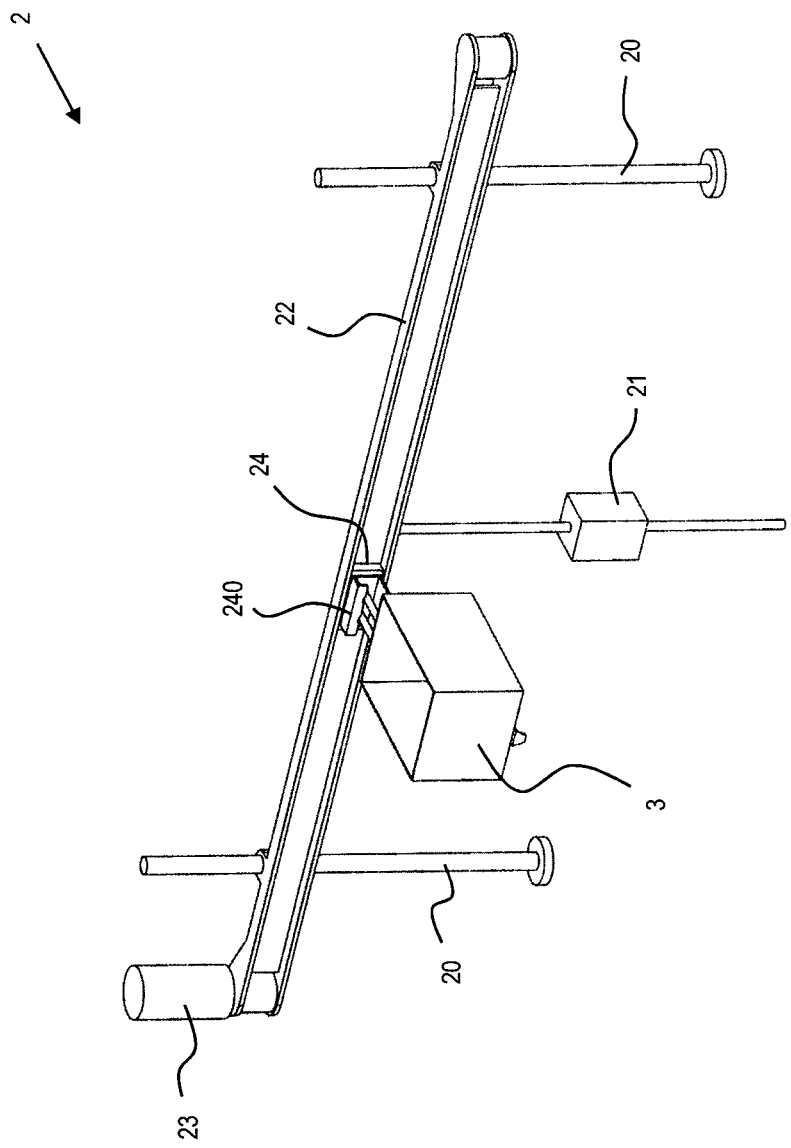
FIG. 4 shows a perspective view of a transport unit of the frying unit of FIG. 1.

FIG. 3 shows a perspective sectional view of the frying unit of FIG. 1. The bottom 10 of the oil pan 1 comprises an offset region, which forms a cold zone 100 below the heating coils 12. The offset region is formed spaced apart from the side walls 11 in the bottom 10. The distance to the side walls 11 forms a circumferential support for the heating coils 12. The terminals of the heating coils 12 are led outward laterally through the side walls 11. The illustrated oil pan 1 is divided into two parts by a partition wall 17 arranged in the middle. The partition wall 17 extends over the entire height of the oil pan 1 and divides it into two pans separate from one another. Each of the pans is connected using a separate fitting to the oil processing unit 4 (only one connecting line of one of the pans is shown). Alternatively, the partition wall can extend only over the height of the side walls 11, but not up into the offset region of the oil pan 1, which forms the cold zone 100, so that the frying oil can circulate unobstructed in the entire cold zone 100. In the case of a low utilization of the frying unit, for example, only a part of the pan can be in operation. The power consumption can thus be reduced. One pan part can be switched off for the processing, i.e., the purification and/or the replacement of the frying oil. When the oil has cooled down sufficiently, the processing/replacement can be performed. Subsequently, the other pan part can be switched off. Basket receptacles 13, 130, in which the baskets 3 can be arranged using corresponding receptacle elements 33, are provided on the inner side of the oil pan 1 on a front side wall (not shown) and on a rear side wall. Upper basket receptacles 13 and lower basket receptacles 130 are provided, wherein the baskets 3 are located in the oil pan 1 when they are arranged in the lower basket receptacle 130 and are located above the oil pan 1 and/or above the frying oil when they are arranged in the upper basket receptacle 13. The baskets 3 can be arranged in the upper basket receptacles 13 for the dripping off of the frying oil. The upper and lower basket receptacles are arranged laterally offset in relation to one another, i.e., they are not arranged one over the other. Each basket receptacle comprises a wedge-shaped recess which tapers from top to bottom. The receptacle elements 33 are arranged in the middle on the bottom 30 of the respective basket 3. They protrude beyond a front or rear side wall 31, respectively, of the basket 3. A holder 32, which can be accommodated by a basket holder 240, is provided in the upper region of the rear side wall on the basket 3. The basket holder 240 is part of the transport unit 2, which is shown exposed in FIG. 4. The transport unit 2 comprises two vertical guides 20, which are arranged spaced apart in relation to one another, a vertical drive 21 in the form of a spindle drive, using which a horizontal guide 22, which is guided using the vertical guides 20, is vertically displaceable. Furthermore, the transport unit 2 comprises a carriage 24, which is guided using the horizontal guide 22 and which is horizontally movable using a horizontal drive 23, in the form of a belt drive. The basket holder 240 is arranged on the carriage 24, which is movable in the vertical and in the horizontal.

Figure 5:
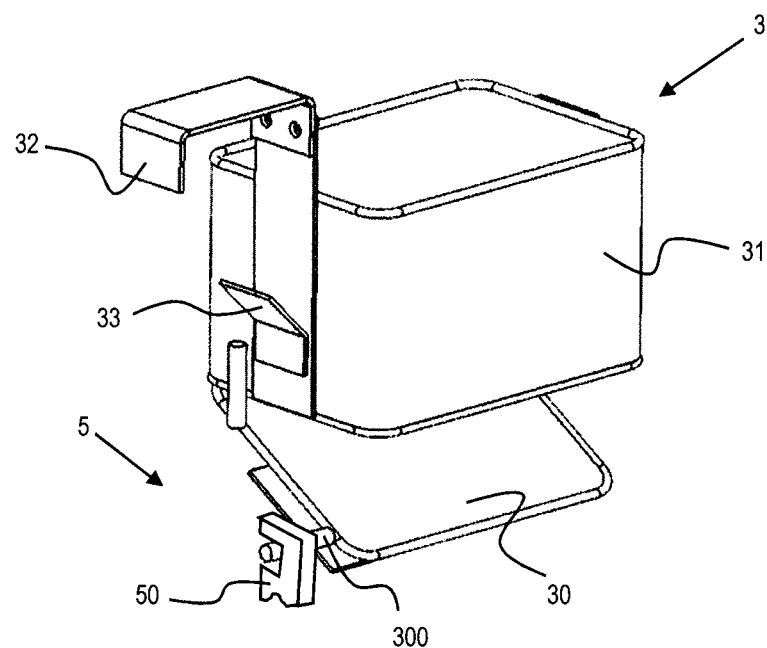
FIG. 5 shows a perspective illustration of a basket of a first embodiment in an emptying unit of a first embodiment.

FIG. 5 shows a perspective illustration of a basket 3 of a first embodiment in an emptying unit 5 of a first embodiment. The basket 3 comprises a bottom 30, which is pivotable downward, and closed circumferential side walls 31. The bottom 30 has a closed circumferential frame, in which a grating is clamped. The bottom 30 is held in the closed position by a spring. Alternatively, the bottom 30 can be held closed using a magnet, for example, using a heat-resistant permanent magnet, for example, using a ferrite magnet. The side walls 31 comprise an upper and a lower closed circumferential frame, between which a grating is clamped. In this embodiment, the holder 32 is formed as a sheet-metal hook, the first leg of which extends from the lower edge of one of the side walls 31 up to beyond the upper edge of this side wall 31. Spaced apart from the upper edge, the sheet metal extends at an angle of 90 degrees, i.e., laterally away from the basket 3, and comprises a downwardly oriented tab on its end facing away from the basket 3. In the lower region of the sheet-metal hook, i.e., in the lower region of the sheet metal of the holder 32, which is arranged between the lower edge and the upper edge of the basket 3, the receptacle element 33 extends inclined laterally upward away from the basket 3, for example, at an angle of 45 degrees. A plate having a receptacle element 33 is also arranged at the same height (not visible in this figure) on the side of the basket 3 opposite to the holder 32. An opener 50 is provided in the emptying unit 5, in which a bolt 300 protruding from the bottom 30 can engage. After the bolt 300 engages in the opener 50, the basket 3 can be raised using the transport unit 2 and possibly also laterally displaced, whereby the bottom 30 can be pivoted downward, whereby the material to be fried located in the basket can be emptied. Alternatively, the basket 3 can be arranged in a stationary manner in the emptying unit 5 and an actuator can move the opener 50 vertically or vertically and horizontally in such a way that the bottom 30 is opened.

Figure 6:
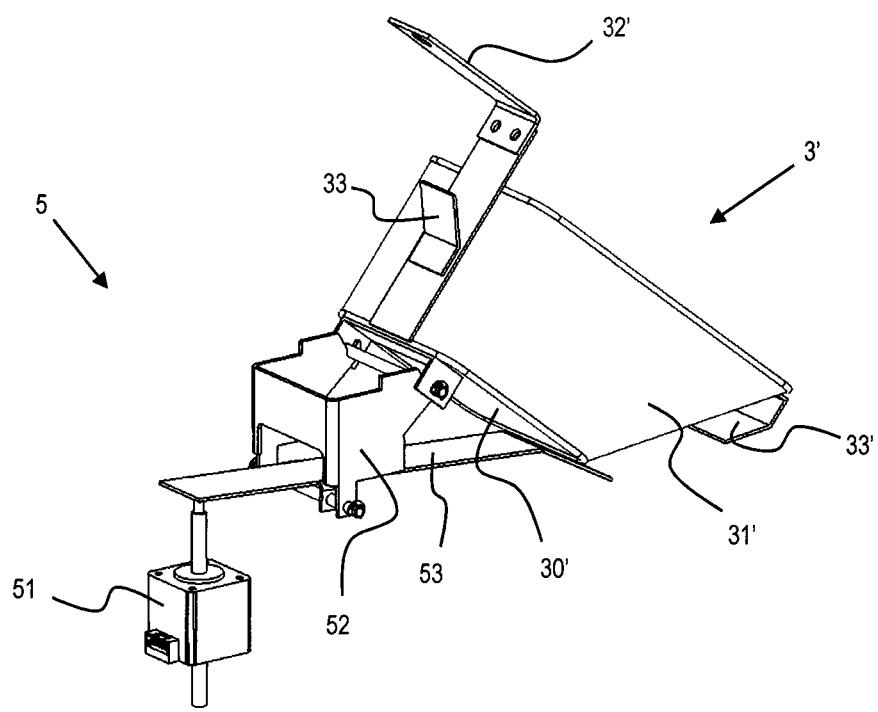
FIG. 6 shows a perspective illustration of a basket of a second embodiment in an emptying unit of a second embodiment.

FIG. 6 shows a perspective illustration of a basket 3' of a second embodiment in an emptying unit 5' of a second embodiment. The basket 3' comprises a bottom 30' connected fixedly to the side walls 31', wherein three of the side walls 31' extend essentially vertically upward from the bottom 30' and one side wall 31' extends at an angle, for example, 45 degrees, upward and outward. A receptacle element 33' is arranged adjoining the upper edge on the inclined side wall. A holder 32' in the form of an angled plate is arranged on the side wall opposite to the inclined side wall, wherein a first leg extends from the lower edge of the basket up to beyond its upper edge and a second leg adjoining the first leg extends essentially horizontally away from the basket. An actuator 51 is provided in emptying unit 5', using which a pivot mechanism 53 is actuatable. The emptying unit 5' comprises a basket receptacle 52 in which the basket 3' is insertable so it is pivotable. The basket 3' can be pivoted using the pivot mechanism 53 around an essentially horizontal axis, wherein the material to be fried located in the basket can be emptied.

Figure 7:
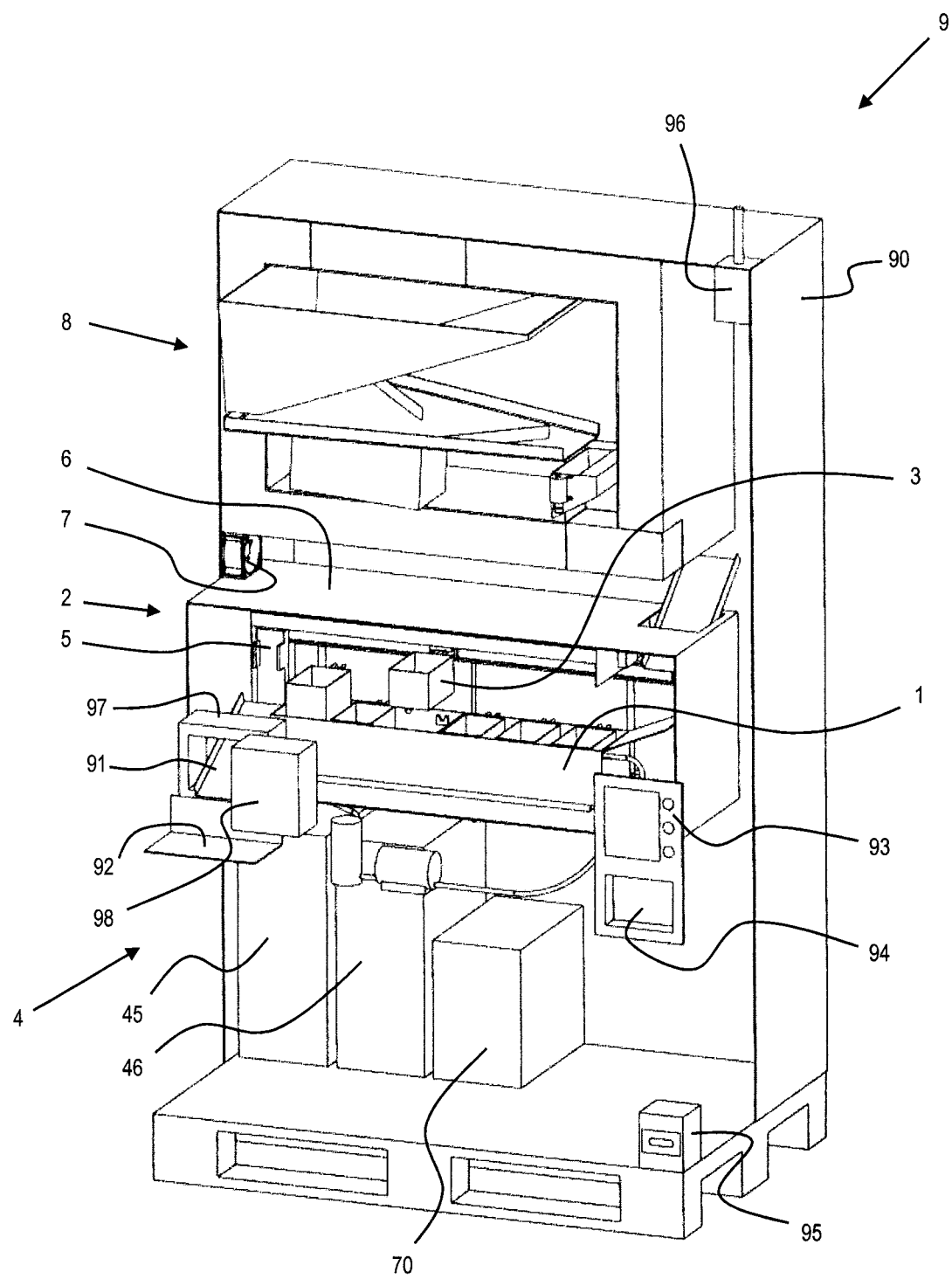
FIG. 7 shows a perspective illustration of a partial sectional view according to the invention of an automatic deep fryer having a frying unit according to the present invention.

FIG. 7 shows a perspective partial sectional view of an automatic deep fryer 9 having a frying unit according to the invention. The automatic deep fryer 9 comprises a housing 90 in which a metering apparatus is arranged in an upper region. The frying unit according to the invention is arranged below the metering apparatus in such a way that material to be fried can move from the metering apparatus to the filling position of the frying unit. Furthermore, the automatic deep fryer 9 comprises a conveyor unit 91 adjoining the frying unit, using which the fried material can be conveyed to the adjoining removal unit 92. An input unit 93 and a payment unit 94 are arranged on the housing exterior, in a region well accessible to a user. A security unit 95 and a transmission unit 96 are arranged in the housing interior. A seasoning unit is provided in the region above the removal unit 91, which can comprise powdered spices, such as salt, pepper, or other spices or spice mixtures, or which can comprise condiments, such as ketchup, mayonnaise, mustard, or other condiments to season the material to be fried therewith. A bowl unit 98 is provided adjacent to the removal unit 91, using which bowls can be supplied to the removal unit 91 to accommodate the material to be fried therein. Furthermore, a napkin dispenser (not shown) can be provided in the automatic deep fryer in the region of the removal unit 92, using which napkins can be supplied to the removal unit 92. The napkin dispenser can be formed combined with the bowl unit 98. A fresh oil container 45 and a usual container 46 are arranged in the automatic deep fryer 9 below the frying unit, i.e., below the oil pan 1, which containers are connected to the oil processing unit 4 by corresponding lines. Using corresponding pumps, fresh oil can be supplied from the fresh oil container 45 to the oil processing unit 4 and used oil can be supplied to the used oil container 46. In this illustration, the frying unit is enclosed by an essentially closed cover 6, in the form of a housing. Openings are only provided in the region of the supply and the discharge of the material to be fried. The ventilation system 7, 70 comprises a fan 7, which is arranged above the frying unit in the housing 90 of the automatic deep fryer 9, and a condensed water container 70, which is arranged below the oil pan 1 adjacent to the oil containers 45, 46. Condensed water lines lead from the frying unit to the condensed water container 70.

LIST OF REFERENCE NUMERALS 1 oil pan
10 bottom
100 cold zone
11 side wall
12 heating element 13 upper basket receptacle
130 lower basket receptacle
14 inlet chute
140 outlet chute
15 drip plate
16 outlet
160 inlet
17 partition wall
2 transport unit
20 vertical guide
21 vertical drive
22 horizontal guide
23 horizontal drive
24 carriage
240 basket holder
3 basket
30 bottom
31 side wall
32 holder
33 receptacle element
4 oil processing unit
40 discharge line
41 filter
42 pump
43 return line
44 sensor
45 fresh oil container
46 used oil container
5 emptying unit
50 opener
51 actuator
52 basket receptacle
53 pivot mechanism
6 cover
7 ventilation system
70 condensed water container
8 metering apparatus
9 automatic deep fryer
90 housing
91 conveyor unit
92 removal unit
93 input unit
94 payment unit
95 security unit
96 transmission unit
97 seasoning unit
98 bowl unit

The invention claimed is:

1. A frying unit, comprising
an oil pan which is open on top;
a transport unit; and
at least one basket,
wherein the at least one basket is movable from a filling position into an interior of the oil pan with the transport unit, and the at least one basket is movable from the interior of the oil pan into an emptying position with the transport unit,
wherein the oil pan is designed in such a way that it can accommodate multiple baskets simultaneously, and the transport unit is designed in such a way that the baskets are movable independently of one another, characterized in that the oil pan comprises basket receptacles, in which the baskets can be accommodated,
wherein the baskets can be arranged above the oil, in upper basket receptacles, which oil is located in the oil pan, and
wherein the baskets can be arranged in the oil, in lower basket receptacles.

2. The frying unit according to claim 1, wherein the oil pan comprises a bottom and side walls which adjoin thereon and are closed per se, and
wherein a heating coil, using the oil which is heatable which is located in the oil pan, is located in the interior of the oil pan, spaced apart from the bottom and the side walls.

3. The frying unit according to claim 1, wherein the transport unit comprises a vertical guide, a vertical drive, and a horizontal guide connected thereto and a horizontal drive, using which a basket holder is movable horizontally and/or vertically, and
wherein a basket is releasably held using the basket holder.

4. The frying unit according to claim 3, wherein the vertical drive and/or the horizontal drive is a drive which is selectable from a group comprising spindle drives, belt drives, chain drives, linear motors, and linear cylinders.

5. The frying unit according to claim 3, comprising at least one basket, wherein the basket comprises a bottom and side walls adjoining thereon and adjoining each other, which are at least partially oil-permeable, wherein a holder is provided at an upper end of the basket, which can be held by the basket holder, and
wherein a receptacle element is provided at a lower end of the basket, which can be accommodated in the basket receptacles.

6. The frying unit according to claim 5, wherein the bottom of the basket is fixedly connected to the side walls or wherein the bottom comprises at least one flap, which is arranged so it is pivotable on one of the side walls.

7. The frying unit according to claim 5, wherein a first side wall comprises at least one flap, which is arranged so it is pivotable on at least one side wall adjacent to the first side wall or is arranged so it is pivotable on the bottom.

8. The frying unit according to claim 1, further comprising an oil processing unit having a discharge line, a filter connected to the discharge line, a pump connected to the filter, and a return line connected to the pump, in which oil can be discharged from the oil pan, filtered, and returned to the oil pan.

9. The frying unit according to claim 1, comprising an emptying unit, in which fried material can be emptied from the basket in the emptying position.

10. The frying unit according to claim 9, wherein the emptying unit comprises a pivot unit, in which the basket is pivotable around an axis or wherein the emptying unit comprises a flap unit, in which at least one flap of the basket is actuatable for opening and/or closing.

11. The frying unit according to claim 1, further comprising a cover, which can be lowered and using which the oil pan can be at least partially covered.

12. The frying unit according to claim 1, further comprising a ventilation unit having a fan, a filter, and/or an oil separator.

13. The frying unit according to claim 1, further comprising a housing, which at least partially encloses components of the frying unit.

14. An automatic deep fryer, comprising
a housing;
a metering apparatus, which is arranged in an upper region of the housing; and a frying unit according to claim 1, which is arranged below the metering apparatus, wherein piece goods which leave the metering apparatus can move to the frying unit.

15. The automatic deep fryer according to claim 14, further comprising
- a conveyor unit;
- a removal unit;
- an input unit;
- a payment unit;
- a security unit; and
- a transmission unit.

16. A method for frying piece goods, the method comprising:
- providing a frying unit according to claim 1;
- moving the basket from an upper basket receptacle above the oil into the filling position;
- filling the basket using piece goods in the filling position;
- moving the basket from the filling position into a lower basket receptacle of the interior of the oil pan using the transport unit;
- frying the piece goods in the basket in the lower basket receptacle of the interior of the oil pan; and
- moving the basket from the lower basket receptacle of the interior of the oil pan into an emptying position using the transport unit.

* * * * *